United States Patent [19]

Schlager

[11] 3,996,278
[45] Dec. 7, 1976

[54] NOVEL 2-AMINOMETHYL-4-,6-DIHALOGEN-PHENOL DERIVATIVES AND METHODS FOR THE PREPARATION THEREOF

[75] Inventor: Ludwig H. Schlager, Vienna, Austria

[73] Assignee: Gerot-Pharmazeutika Dr. Walter Otto K.G., Vienna, Austria

[22] Filed: Jan. 2, 1974

[21] Appl. No.: 429,984

[30] Foreign Application Priority Data

Jan. 2, 1973  Austria ................. 173/73
Aug. 24, 1973  Austria ................. 7387/73

[52] U.S. Cl. .............. 260/559 R; 260/247.2 H; 260/247.7 R; 260/268 C; 260/293.76; 260/559 B; 260/559 H
[51] Int. Cl.$^2$ .................... C07C 103/32
[58] Field of Search ....... 260/559 R, 559 H, 559 B, 260/570.9

[56] References Cited

UNITED STATES PATENTS 3,809,721  5/1974  Schultz et al. ............. 260/570.9

FOREIGN PATENTS OR APPLICATIONS 1,190,066  8/1972  France
2,119,067  8/1972  France

OTHER PUBLICATIONS

Noller, Chem. of Org. Compds., 3rd Ed., W. B. Saunders Co., (1965), p. 552.

Primary Examiner—C. Davis
Attorney, Agent, or Firm—Sughrue, Rothwell, Mion, Zinn & Macpeak

[57] ABSTRACT 2-aminomethyl-4,6-dihalogenphenol derivatives and salts thereof with physiologically acceptable acids or bases having the formula:

wherein X is the same halogen in both positions, $R_1$ is a hydrogen atom or a lower alkyl group, $R_2$ is an alkyl, cycloalkyl, aryl or aralkyl group, or $R_1$ and $R_2$ together with the nitrogen atom may form a saturated heterocyclic ring, which ring may be interrupted by an oxygen, nitrogen or sulfur atom, $R_3$ is a hydrogen atom, an alkyl, alkoxyalkyl, carboxyalkyl, carbamylalkyl, aralkyl, acyl or sulfonyl group or a base radical, e.g. an alkali metal atom, and $R_3''$ is a cyanoalkyl, hydroxyalkyl, carbalkoxy-alkyl, N,N-dialkylcarbamyl, N-alkylcarbamyl-alkyl or N,N-dialkylcarbamylalkyl group, are useful as diuretics and saluretics; some derivatives possess secretolytic activity.

16 Claims, No Drawings

NOVEL 2-AMINOMETHYL-4-,6-DIHALOGENPHENOL DERIVATIVES AND METHODS FOR THE PREPARATION THEREOF

BACKGROUND OF THE INVENTION

1. Field of the Invention

The invention relates to novel 2-aminomethyl-4,6-dihalogenphenol derivatives and a method for preparing the same.

2. Description of the Prior Art

Principally an aminomethylation of halogen phenols is known (Journ. Am. Chem. Soc. 74, 1518 (1952)). With respect to 2,4-dihalogen phenols also an amidomethylation, that means a "Tscherniac-Einhorn" reaction is described (see German Published Application No. 2,163,911).

SUMMARY OF THE INVENTION

According to the invention, there is provided a class of novel 2-aminomethyl-4,6-dihalogen-phenol derivatives and salts thereof with physiologically acceptable acids or bases having the formula:

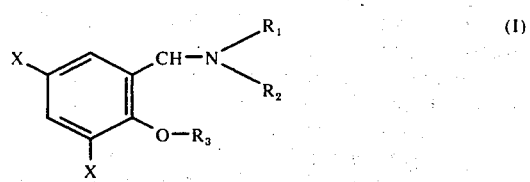

wherein X is the same halogen in both positions, $R_1$ is a hydrogen atom or a lower alkyl group, $R_2$ is an alkyl, cycloalkyl, aryl or aralkyl group, or $R_1$ and $R_2$ together with the nitrogen atom may form a saturated heterocyclic ring, which ring may be interrupted by an oxygen, nitrogen or sulfur atom, and $R_3$ is a hydrogen atom, an alkyl, alkoxyalkyl, carboxyalkyl, carbamylalkyl, aralkyl, acyl or sulfonyl group or a base radical, e.g. an alkali metal atom.

The invention also provides a method for preparing these compounds.

According to the invention the novel compounds are prepared by a method which comprises reacting a 2,4-dihalogenphenol of the formula:

wherein X is as defined above with formaldehyde and an amine of the formula:

wherein $R_1$ and $R_2$ are as defined above, preferably in an inert solvent, and either converting the obtained 2-aminomethyl-4,6-dihalogenphenol of the formula:

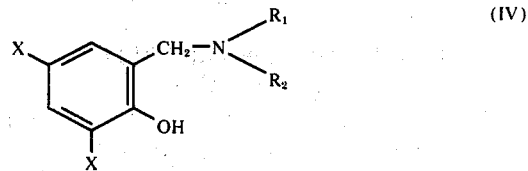

wherein X, $R_1$ and $R_2$ are as defined above immediately in its salts with physiologically acceptable acids or bases or synthesizing the corresponding O-substituted derivatives of formula (I) by further reacting the free phenolic component (IV) or its alkali phenolate resp. with a compound of the formula:

$$Y - R_3' \qquad (V)$$

wherein $R_3'$ has the same meaning like $R_3$ with exception of hydrogen or base radical and Y is a reactive group, preferably a halogen atom, and optionally converting said O-substituted derivatives in a salt thereof.

According to the invention there is provided also a class of novel 2-aminomethyl-4,6-dihalogen-phenol derivatives and salts thereof with physiologically acceptable acids having the formula:

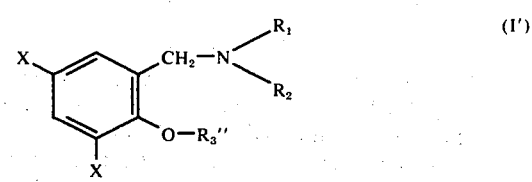

wherein X, $R_1$ and $R_2$ are as defined above and $R_3''$ may be a cyanoalkyl, hydroxyalkyl, carbalkoxyalkyl, N,N-dialkylcarbamyl, N-alkylcarbamyl-alkyl or N,N-dialkylcarbamyl-alkyl group.

According to the invention, the novel compounds of formula (I') are prepared by a method which comprises reacting compounds of formula (I), wherein $R_3$ is a hydrogen atom or a base radical (e.g. alkali) with compounds of the formula:

$$Y - R_3'' \qquad (V'')$$

wherein $R_3''$ is as defined above and Y is a reactive group, preferably a halogen atom.

It is advantageous to carry the reactions as described below in aprotic solvents, e.g. hexamethylphosphoric acid triamide, under mild conditions (room temperature up to about 60° C). Thus, good yields are obtained. A possible competitive reaction of a quaternisation of the group

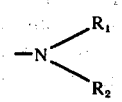

practically does not occur with the reaction conditions of the invention.

The compounds according to the invention (I) and (I') have pharmaceutically useful properties. The hydrochlorides thereof dissolve mostly easily in water and also in chloroform, so that said compounds have balanced hydrophilic and lipophilic properties. Especially those derivatives carrying a N,N-dialkylcarbamyl-alkyl group in the position of $R_3''$ show highly diuretic and saluretic activity; some of the derivatives also possess a secretolytic activity.

DESCRIPTION OF THE PREFERRED EMBODIMENTS

The following examples describe the preparation of the present compounds using the methods of the invention without, however, limiting the scope of the invention thereto.

EXAMPLE 1

453 g of N-methylcyclohexylamine are dropped to a mixture of 300 ml of formaldehyde (35%) and 2 l dioxane, cooled to 10° C, with stirring. Then 1008 g of dibromophenol are added to the mixture. The obtained mixture is heated for 3 hours under reflux and then evaporated in vacuo, until a syrupy consistence is obtained. By diluting the brown syrup with methanol and scratching the cooled solution crystalline N-(2-hydroxy-3,5-dibromobenzyl)-N-methylcyclohexylamine, m.p. 65° – 67° C, is obtained, which is washed with methanol on a filter.

The hydrochloride of this compound is obtained from the mother liquor after adding alcoholic HCl-solution. After recrystallization from ethanol the hydrochloride melts at 182° – 186° C.

EXAMPLE 2

6,08 g of lithium amide are added in portions to a solution of 100 g of the base obtained according to Example 1 in 150 ml of dimethylformamide with stirring. The temperature of the mixture rises to 40° C. Soon a colorless powder precipitates from the clear solution, which is the lithium phenolate of the used compound, m.p. 130° C.

EXAMPLE 3

105 ml of a solution of 29% sodium methylate are dropped to a solution of 200 g of the base obtained according to Example 1 in 600 ml of acetone with stirring. Then the solution is evaporated in vacuo and the remainder is stirred with ether, thereby crystallizing the sodium phenolate of the used compound, m.p. 200° – 203° C.

EXAMPLE 4

A solution of 8,6 g of acetylchloride in 20 ml chloroform is dropped into a stirred solution of 37,7 g of the base obtained according to Example 1 in 100 ml chloroform. The temperature of the mixture rises to 40° C thereby. Then the mixture is heated for 30 minutes with reflux, the cooled solution is extracted with water, dried over $Na_2SO_4$ and evaporated in vacuo. The remainder is taken up in a small amount of isopropanol. By adding alcoholic HCl and ether to this solution the hydrochloride of N-(2-acetoxy-3,5-dibromobenzyl)-N-methylcyclohexylamine precipitates, melting after recrystallization from ethanol at 188° – 192° C.

EXAMPLE 5

7,66 g of the lithium phenolate obtained according to Example 2 are dissolved in 300 ml of dimethylformamide. A solution of 3,43 g of ethyl iodide in 10 ml of dimethylformamide is dropped thereto with stirring. After 2 hours the reaction mixture is heated to 50° C and maintained for 1 hour at this temperature. Then the solvent is evaporated in vacuo. The remainder is taken up in chloroform, extracted with water and the dried chloroform solution is evaporated. Treating the remainder with alcoholic HCl solution gives the crystalline hydrochloride of N-(2-ethoxy-3,5-dibromobenzyl)-N-methylcyclohexylamine, melting at 205° C after crystallization from ethanol.

EXAMPLE 6

A mixture of 95 ml of 35% formaldehyde solution and 100 ml of dioxane is dropped into a solution of 80 g of tertiary butylamine in 350 ml of dioxane, cooled to 15° C, with stirring. The mixture is allowed to stand over night, then heated to 80° C. In the course of 4 hours a solution of 252 g of 2,4-dibromophenol in 250 ml of dioxane is dropped thereto, precipitating thereby the main charge of the reaction product. 1 hour after completion of this addition it is cooled, the precipitate is sucked off, washed with ethanol on the filter and dried. By concentrating the dioxane-mother liquor and the alcoholic washing liquid further material is obtained. Remaining reaction product precipitates from the dioxane concentrate in form of the hydrochloride by heating with alcoholic HCl. The hydrochloride is converted in $H_2O/CHCl_3$ in the free base with $HaHCO_3$. Total yield = 268 g (79,5% of the theory). Recrystallization from acetic ester yields the N-(2-hydroxy-3,5-dibromobenzyl)-tert.butylamine in form of colorless felted needles, melting at 173° – 175° C.

EXAMPLE 7

4 ml of sodium methylate solution (29%) are dropped to a suspension of 6,74 g of the base obtained according to Example 6 in 10 ml of hexamethylphosphoric acid triamide (HMPT) with stirring. Thus, a yellowish solution is obtained. Said solution is heated to 40° C. In the course of 3 hours a solution of 3 g of benzylchloride in 5 ml of HMPT is dropped thereto. The stirring is continued 3 hours at a temperature of 40° C. Then the cooled mixture is added to 200 ml of an icecold aqueous NaCl solution and extracted with ether several times. The combined ether extracts are extracted with 0,1N NaOH and then with $H_2O$, dried over $Na_2SO_4$, stirred with charcoal and filtered. By adding alcoholic HCl to the filtrate the hydrochloride of N-(2-benzyloxy-3,5-dibromobenzyl)-tert. butylamine precipitates. It is recrystallized from ethanol and melts at 204° – 208° C. Yield = 7,9 g (85,4% of the theory).

In analogy to the methods described in the above Examples further derivatives of formula (I) are obtained. They are summarized in the following Table 1.

Table 1

| X | $R_1$ | $R_2$ | $R_3$ | m.p. ° C free base | m.p. ° C hydrochloride |
|---|---|---|---|---|---|
| Br | $CH_3$ | cyclohexyl | $CO.CH_2.C_6H_5$ | | 153 – 157 |
| Br | $CH_3$ | cyclohexyl | $SO_2.C_6H_4.CH_3(p)$ | 94 – 96 | |
| Br | $CH_3$ | cyclohexyl | $SO_2.CH_3$ | | 198 – 203 |
| Br | $CH_3$ | cyclohexyl | $CO.CH_2.O.CO.CH_3$ | | 161 – 168 |

Table 1-continued

| X | $R_1$ | $R_2$ | $R_3$ | m.p. °C free base | m.p. °C hydrochloride |
|---|---|---|---|---|---|
| Br | $CH_3$ | cyclohexyl | $CH_2.C_6H_5$ | | 131 – 134 |
| Br | $CH_3$ | cyclohexyl | $CH_3$ | | 185 – 192 |
| Br | $CH_3$ | cyclohexyl | $(CH_2)_2.O.C_2H_5$ | | 142 – 144 |
| Br | $CH_3$ | cyclohexyl | $CH_2.CO.NH_2$ | 127 – 128 | |
| Br | $CH_3$ | cyclohexyl | $CH_2COOH$ | | 178 – 184 |
| Br | $CH_3$ | cyclohexyl | $CH_2.C_6H_4.Cl(o)$ | | 132 – 135 |
| Br | $CH_3$ | cyclohexyl | $CH_2.C_6H_4.Cl(p)$ | | 165 – 167 |
| Cl | $CH_3$ | cyclohexyl | H | 55 – 57 (Na-salt: m.p. 170–175° C) | 182 – 184 |
| Cl | $CH_3$ | cyclohexyl | $CH_2COOH$ | | 176 – 186 |
| Cl | $CH_3$ | cyclohexyl | $COCH_3$— | | 182 – 188 |
| Cl | $CH_3$ | cyclohexyl | $CO.CH_2.C_6H_5$ | | 144 – 150 |
| Cl | $CH_3$ | cyclohexyl | $CH_2.C_6H_5$ | | 163 – 167 |

| X | $-N\begin{smallmatrix}R_1\\R_2\end{smallmatrix}$ | $R_3$ | m.p. °C free base | m.p. °C hydrochloride |
|---|---|---|---|---|
| Br | 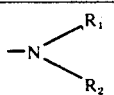 morpholino | H | 85 – 87 (Na-salt: m.p.228–231° C) | 185 – 191 |
| Br | 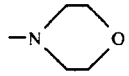 morpholino | $COCH_3$ | | 193 – 199 |
| Br | 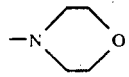 morpholino | $CH_2.C_6H_5$ | | 184,5 – 186,5 |
| Br | 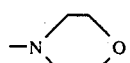 morpholino | $CH_2.C_6H_4.Cl(o)$ | | 188 – 195 |
| Br | 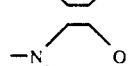 N-methylpiperazino | H | 104 (Na-salt: m.p. >300° C) | dihydrochloride 212 – 216 |
| Br | 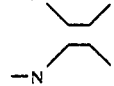 N-methylpiperazino | $COCH_3$ | | 201 – 208 |
| Br | 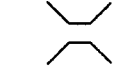 N-methylpiperazino | $CH_2C_6H_5$ | 127 – 130 | 189 – 196 |
| Br | 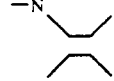 N-hydroxyethylpiperazino | H | 98 – 104 (Na-salt: m.p.246–249° C) | |
| Br | 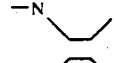 N-hydroxyethylpiperazino | $CH_2.C_6H_4Cl(o)$ | | 179 – 183 |
| Br | 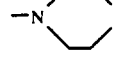 piperidino | H | 100 – 101 (Na-salt: m.p.250–255° C) | |
| Br | 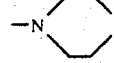 piperidino | $CH_2.C_6H_5$ | | 176 – 179 |

EXAMPLE 8

A solution of 6,4 g of chloroacetic acid dimethylamide in 10 ml of HMPT is dropped to a suspension of 20 g of the sodium salt of N-(2-hydroxy-3,5-dibromobenzyl)-N-methylcyclohexylamine in 20 ml of hexamethylphosphoric acid triamide (HMPT) for 3 hours at 40° C with stirring. The reaction is continued for 1 hour at 40° C. Then the mixture is cooled and stirred for 250 ml of an icecold saturated aqueous saline solution. The syrupy mass precipitated thereby is dissolved in diethyl ether (after decanting the aqueous phase), the solution is extracted with diluted NaOH and then with water, dried over $Na_2SO_4$ and after filtration alcoholic HCl solution is added. Thus, a syrupy hydrochloride is precipitated, which crystallizes after decanting the ether solution by boiling with $CCl_4$. The hydrochloride of N-[2-(N',N'-dimethylcarbamylmethoxy)-3,5-dibromobenzyl]-N-methyl-cyclohexylamine melts at 107° – 113° C after recrystallization from acetone/$CCl_4$. After recrystallization from acetone-ether the melting point rises to 132° – 136° C.

EXAMPLE 9

7,5 g of chloroacetonitrile are dropped to a suspension of 20 g of the sodium salt of N-(2-hydroxy-3,5-dibromobenzyl)-N-methyl-cyclohexylamine in 30 ml of HMPT at room temperature with stirring. After 5 hours the reaction mixture is stirred with 250 ml of icecold saturated aqueous saline. The aqueous phase is decanted from the precipitated product, the latter is taken up with $CHCl_3$. The chloroform solution is dried over $Na_2SO_4$, filtered and evaporated. By adding alcoholic HCl solution to the remainder and diluting with acetone the hydrochloride of N-(2-cyanomethoxy-3,5-dibromobenzyl)-N-methylcyclohexylamine is precipitated. This product is recrystallized from isopropanol and melts then at 186° – 189° C.

According to the methods of Examples 8 and 9 further derivatives are obtained, which are summarized in the following Table 2.

Table 2

| X | $R_1$ | $R_2$ | $R_3$ | m.p. ° C hydrochloride |
|---|---|---|---|---|
| Br | $CH_3$ | cyclohexyl | $CH_2COOC_2H_5$ | 138 – 145 |
| Br | $CH_3$ | cyclohexyl | $CH_2CH_2.OH$ | 160 – 166 |
| Br | $CH_3$ | cyclohexyl | $CH_2CO.N(C_2H_5)_2$ | 152 – 157 |
| Br | $CH_3$ | cyclohexyl | $CO.N(C_2H_5)_2$ | 175 – 185 |
| Cl | $CH_3$ | cyclohexyl | $CH_2COOC_2H_5$ | 143 – 146 |
| Cl | $CH_3$ | cyclohexyl | $CH_2CO.N(C_2H_5)_2$ | 150 – 153 |

| X | $-N\langle{}^{R_1}_{R_2}$ | $R_3$ | m.p.° C hydrochloride |
|---|---|---|---|
| Br | morpholino | $CH_2COOC_2H_5$ | 150 – 157 |
| Br | 4-(2-hydroxyethyl)piperazino | $CH_2COOC_2H_5$ | 183 – 187 |

Having thus described my invention, what I desire to secure by Letters Patent and hereby claim is:

1. A compound of the formula:

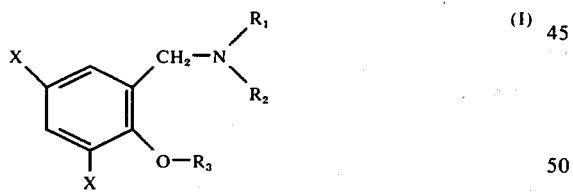

(I)

wherein X is the same halogen in both positions, $R_1$ is a hydrogen atom or a lower alkyl group, $R_2$ is an alkyl, cycloalkyl, aryl or aralkyl group, or $R_1$ and $R_2$ together with the nitrogen atom may form a saturated heterocyclic ring, which ring may be interrupted by an oxygen, nitrogen or sulfur atom, and $R_3$ is carboxylalkyl, carbamylalkyl, acyl, carbalkoxyalkyl, N,N-dialkylcarbamyl, N-alkylcarbamyl-alkyl or N,N-dialkylcarbamylalkyl group and salts thereof with physiologically acceptable acids or bases.

2. A compound as claimed in claim 1 wherein X is bromine, $R_1$ is methyl, $R_2$ is cyclohexyl and $R_3$ is $CH_2CO.N(CH_3)_2$.

3. A compound is claimed in claim 1 wherein X is bromine, $R_1$ is methyl, $R_2$ is cyclohexyl and $R_3$ is $CH_2CO.N(C_2H_5)_2$.

4. A compound as claimed in claim 1 wherein X is chlorine, $R_1$ is methyl, $R_2$ is cyclohexyl and $R_3$ is $CH_2CO.N(C_2H_5)_2$.

5. A compound as claimed in claim 1 wherein X is bromine, $R_1$ is $CH_3$, $R_2$ is cyclohexyl and $R_3$ is $CH_2COOC_2H_5$.

6. A method of preparing compounds of the formula:

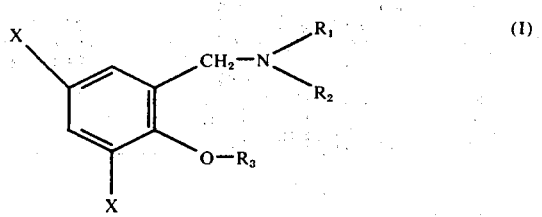

(I)

wherein X is the same halogen in both positions, $R_1$ is a hydrogen atom or a lower alkyl group, $R_2$ is an alkyl, cycloalkyl, aryl or aralkyl group, or $R_1$ and $R_2$ together with the nitrogen atom may form a saturated heterocyclic ring, which ring may be interrupted by an oxygen, nitrogen or sulfur atom, and $R_3$ is carboxyalkyl, carbamylalkyl, acyl, carbalkoxyalkyl, N,N-dialkylcarbamyl, N-alkylcarbamyl-alkyl or N,N-dialkylcarbamylalkyl group and salts thereof with physiologically acceptable acids or bases, said method comprising reacting a 2,4-dihalogenphenol of the formula:

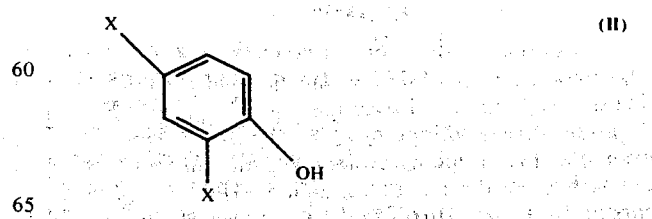

(II)

wherein X is as defined above with formaldehyde and an amine of the formula:

wherein $R_1$ and $R_2$ are as defined above to obtain a 2-amino-methyl-4,6-dihalogenphenol of the formula:

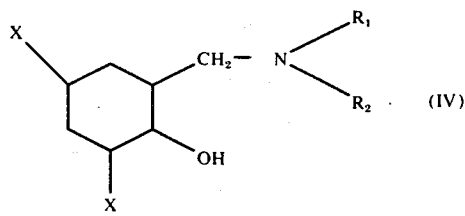

and synthesizing the corresponding O-substituted derivatives of the formula (I) by further reacting the free phenolic component (IV) or its alkali phenolate with a compound of the formula:

$$Y - R_3' \qquad (V)$$

wherein $R_3'$ has the same meaning as $R_3$ and Y is a reactive group splittable from said $R_3'$ during said reaction with said compound of the formula (IV).

7. The method of claim 1 of preparing compounds of the formula:

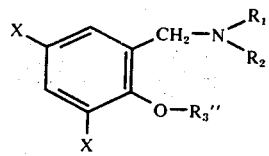

wherein X, $R_1$ and $R_2$ are as defined in claim 6 and $R_3''$ is a carbalkoxyalkyl, N,N-dialkylcarbamyl, N-alkylcarbamyl-alkyl or N,N-dialkylcarbamylalkyl group.

8. The method of claim 7, wherein the reaction between the compound of the formula (IV) and the compound of the formula (V) is carried out in an aprotic solvent or an inert solvent mixture containing at least one aprotic solvent.

9. The method of claim 8, wherein the reaction is carried out in the presence of a basic condensing agent.

10. The process of claim 6 wherein said reaction between the compound of the formula (II) with formaldehyde and the amine of the formula (III) is carried out in an inert solvent.

11. The process of claim 6 wherein Y is a halogen atom.

12. The process of claim 6 wherein said compound of the formula (I) is converted to a physiologically acceptable salt thereof with a physiologically acceptable acid or base.

13. The process of claim 12 wherein $R_3$ is a carbalkoxyalkyl, N,N-dialkylcarbamyl, N-alkylcarbamyl-alkyl or N,N-dialkylcarbamylalkyl group.

14. The method of claim 9, wherein the basic condensing agent is selected from the group consisting of sodium methylate, triethylamine and sodium hydride.

15. The method of claim 7, wherein the reaction between the compound of the formula (IV) and the compound of the formula (V) is carried out in the presence of a basic condensing agent.

16. The process of cliam 15, wherein the basic condensing agent is selected from the group consisting of sodium methylate, triethylamine and sodium hydride.

* * * * *

UNITED STATES PATENT AND TRADEMARK OFFICE
CERTIFICATE OF CORRECTION

PATENT NO. : 3,996,278
DATED : December 7, 1976
INVENTOR(S) : Ludwig H. SCHLAGER It is certified that error appears in the above-identified patent and that said Letters Patent are hereby corrected as shown below:

IN THE HEADING:

The claimed Priority Data is incorrect. Should read:

Jan. 2, 1973    Austria................... 1/73
Aug. 24, 1973   Austria............... 7387/73

Signed and Sealed this

Fifth Day of April 1977

[SEAL]

Attest:

RUTH C. MASON
Attesting Officer

C. MARSHALL DANN
Commissioner of Patents and Trademarks